(12) United States Patent
Maswadi

(10) Patent No.: US 10,786,158 B2
(45) Date of Patent: Sep. 29, 2020

(54) OPTOACOUSTIC / PHOTOACOUSTIC / ACOUSTIC IMAGING SYSTEM USING PROBE BEAM DEFLECTION

(75) Inventor: Saher Maswadi, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 96 days.

(21) Appl. No.: 13/514,160

(22) PCT Filed: Dec. 10, 2010

(86) PCT No.: PCT/US2010/059831
§ 371 (c)(1),
(2), (4) Date: Nov. 4, 2012

(87) PCT Pub. No.: WO2011/072198
PCT Pub. Date: Jun. 16, 2011

(65) Prior Publication Data
US 2013/0041247 A1 Feb. 14, 2013

Related U.S. Application Data

(60) Provisional application No. 61/285,394, filed on Dec. 10, 2009.

(51) Int. Cl.
*A61B 8/00* (2006.01)
*A61B 5/00* (2006.01)
*G01H 9/00* (2006.01)

(52) U.S. Cl.
CPC .......... *A61B 5/0097* (2013.01); *A61B 5/0095* (2013.01); *A61B 8/4281* (2013.01); *A61B 8/4483* (2013.01); *G01H 9/00* (2013.01)

(58) Field of Classification Search
CPC ....... A61B 6/00; A61B 5/0095; A61B 8/4281; A61B 8/4483; A61B 5/0093; A61B 5/0097; G01H 9/00; G02F 1/11; G01S 15/8968
USPC .................................................. 600/407–480
See application file for complete search history.

(56) References Cited

U.S. PATENT DOCUMENTS

| | | | | |
|---|---|---|---|---|
| 3,790,252 A | * | 2/1974 | Pao | 359/299 |
| 4,363,533 A | * | 12/1982 | Stowe | G02F 1/0134 367/141 |
| 4,468,136 A | * | 8/1984 | Murphy | G01N 21/171 250/334 |
| 5,615,675 A | * | 4/1997 | O'Donnell et al. | 600/425 |
| 5,818,809 A | * | 10/1998 | Arai et al. | 369/112.24 |
| 6,466,806 B1 | | 10/2002 | Geva et al. | 60/310 |
| 6,552,841 B1 | | 4/2003 | Lasser et al. | 359/305 |

(Continued)

FOREIGN PATENT DOCUMENTS

WO   WO 2009023173   *   2/2009   ............ G01N 21/35

OTHER PUBLICATIONS

Sell et al., "Photoacoustic and Photothermal Beam Deflection as a Probe of Laser Ablation of Materials", J. Appl. Phys. 69 (3), Feb. 1, 1991; pp. 1330-1336. (Year: 1991).*

(Continued)

*Primary Examiner* — James M Kish
(74) *Attorney, Agent, or Firm* — Norton Rose Fulbright US LLP

(57) ABSTRACT

Embodiments of the invention are directed to a non-contact optical method using a probe beam deflection technique (PBDT) to detecting acoustic waves transiting an acoustic coupling medium.

17 Claims, 13 Drawing Sheets

(56) References Cited

U.S. PATENT DOCUMENTS

| | | | | |
|---|---|---|---|---|
| 6,771,412 | B2* | 8/2004 | Torchigin | G02F 1/125 359/285 |
| 7,393,325 | B2* | 7/2008 | Barthe | A61N 7/022 600/437 |
| 2002/0072661 | A1* | 6/2002 | Wiesmann et al. | 600/328 |
| 2002/0085594 | A1* | 7/2002 | Pezeshki | G02B 6/32 372/20 |
| 2002/0180979 | A1* | 12/2002 | Chou | G01N 21/553 356/484 |
| 2003/0174329 | A1* | 9/2003 | Kuper et al. | 356/399 |
| 2003/0231294 | A1* | 12/2003 | Wariar et al. | 356/39 |
| 2005/0024587 | A1* | 2/2005 | Somani | 351/214 |
| 2005/0057736 | A1* | 3/2005 | Tani | G03F 7/70375 355/55 |
| 2005/0217381 | A1 | 10/2005 | Falk | 73/596 |
| 2008/0068721 | A1* | 3/2008 | Murnan | G02B 17/04 359/629 |
| 2008/0204719 | A1* | 8/2008 | Trainer | 356/73 |
| 2012/0002193 | A1* | 1/2012 | Elliott | G01K 17/003 356/121 |

OTHER PUBLICATIONS

Tjin et al., "Factors Influencing the Depth of Penetration of He-Ne Laser in Whole Blood", Proc. SPIE 1067, Optical Fibers in Medicine IV, (Jun. 15, 1989), pp. 94-97. (Year: 1989).*

Poddar et al., "Non-Invasive Glucose Monitoring Techniques: A review and current trends", Oct. 31, 2008, Dissertation Shri G S Institue and Nayang Technological University; pp. 1-47. (Year: 2008).*

Zapka et al., "Photoacoustic pulse generation and probe-beam deflection for ultrasonic velocity measurements in liquids", Appl. Phys. Lett. 40(4), Feb. 15, 1982, pp. 310-312. (Year: 1982).*

International Search Report and Written Opinion in International Application No. PCT/US2010/059831 dated Jul. 28, 2011.

International Preliminary Report on Patentability in International Application No. PCT/US2010/059831 dated Jun. 12, 2012.

* cited by examiner

OPTOACOUSTIC / PHOTOACOUSTIC / ACOUSTIC IMAGING SYSTEM USING PROBE BEAM DEFLECTION

This application is a U.S. National stage application under 35 USC 371 of International Application No. PCT/US2010/059831 filed Dec. 10, 2010, which claims priority to U.S. Provisional Application No. 61/285,394 filed Dec. 10, 2009. This application claims priority to each of the above referenced applications and the entire contents of each of the above-referenced disclosures is incorporated herein by reference in its entirety.

This application claims priority to U.S. Provisional Patent Application Ser. No. 61/285,394 filed Dec. 10, 2009, which is incorporated herein by reference in its entirety.

BACKGROUND OF THE INVENTION

I. Field of the Invention

Embodiments of this invention are directed generally to biology and medicine. Certain embodiments are directed to detecting acoustic waves by using electromagnetic probe beams.

II. Background

In biomedical optoacoustics, tissue is illuminated with short laser pulses. The light is scattered inside the tissue and heats (by degrees or a fraction of a degree) absorbing structures such as foreign bodies. Because of the thermoelastic effect, the heating generates pressure transients exactly representing the absorbing structures. These ultrasound transients propagate to the tissue surface and are measured with an acoustic transducer.

A key element of every optoacoustic system is the ultrasound transducer. Classically ultrasound transducers are made from piezoelectric materials, which allow a direct conversion of pressure into voltage. Piezoelectric materials, such as Lead Zirconate Titanate (PZT), and Polyvinylidene Fluoride (PVDF) have high conversion efficiency. Medical ultrasound applications have motivated development of linear and even two-dimensional arrays. Manufacturing difficulties, however, limit the minimum element size and element number of such probes.

There remains a need for more efficient transduction of acoustic energy for imaging. The present invention provides additional methods and apparatus for detecting acoustic energy.

SUMMARY OF THE INVENTION

The limitations of acoustic transducers described above have encouraged the development of new optical methods for imaging with high sensitivity and resolution to provide two and/or three-dimensional images. The probe beam deflection technique (PBDT), a non-contact optical method, is used to record the optoacoustic signals in an acoustic cell that is acoustically coupled to a target. In U.S. Pat. No. 4,468,136 PBDT is used to detect a static lens produced by a refractive index gradient generated by the heating and expansion of a sample as a result of absorbed laser radiation. Embodiments of the current invention go beyond this static thermal lens methodology and provide the capability of detecting acoustic waves transiting an acoustic coupling medium. In certain aspects, the pressure amplitude of an acoustic wave, the distance of the acoustic wave from its source, and the angular direction of the acoustic wave can be determined using the methods and apparatus of the current invention. The ability of a single probe to measure the angle the acoustic signal is traveling from its source is unique and can be employed to provide a higher resolution image.

In certain aspects, the optical probe beam has a wide field of view since it can sense the pressure wave passing from any direction around its axis of propagation. An imaging system can be designed with fast or real-time images by reducing the scanning time (depending on the signal acquisition and imaging software). In certain aspects sufficient resolution of an imaging object may require scanning the acoustic waveforms around the object. Scanning time depends on the number of sensors used and the speed of scanning. The speed of scanning can be reduced (e.g., to a single time point) by using higher number of probes covering the target area. In a further aspect using high frequency pulse laser excitation laser will speed up the process. The scanning time will also depend on the acquisition system and the signal processing. However the ability to design and develop sensor head based on the probe beam defection technique at different layers in three dimension X, Y and Z coordinate above the object in remote fashion where intersection of probes is possible in high number of 5 to 100 sensor per layer or even more reduces the scanning time or even become a real time with no need of scanning.

In a further aspect, high resolution imaging system can comprise multi-probes with a probe beam diameter of at least, about, or at most 5, 10, 20, 30, 40, 50, to 20, 30, 40, 50, 60, 70, 80, 90 μm or more, including all values and ranges there between. The more probes and the smaller the spacing between them the faster the system becomes and the higher the resolution. In certain aspects the probe beams can spaced at 200, 300, 400, 500, 600, 700, 800, 900, 1,000, 2,000, 3,000, 4,000, 5,000 μm or more including all values and ranges there between. In further aspects the probe beams can be spaced at 1, 2, 3, 4, 5, 6, 7, 8, 9, 10 or more mm or cm including all values and ranges there between.

In still further aspects, the spatial resolution can be enhanced by using the angular information and smaller spot size of the probe beam. Also the acoustic speed of the medium can be modified to enhance resolution. The basic formula of time resolution is ($\Delta t$=beam waist/speed of sound at the medium) e.g. 50 μm focused probe beam in water with speed of sound 1500 m/s the time resolution will be 33 ns. In other examples using Glycerol (glycerine) as the coupling medium where the probe propagates at 1900 m/s speed of sound for the same 50 μm focused probe beam, the time resolution will be 26 ns. In addition of finding the suitable coupling medium where the probe beam propagates through, the probe beam wavelength is an important factor, higher resolution can be improved by using shorter wavelength, such as using blue ray light where smaller focus spot size can be achieved compared to red light. Optimizing resolution and sensitivity depends on the imaging application. In certain aspects the coupling medium will have a homogenous acoustic speed throughout the medium. In other aspects the coupling medium is engineered to have variable acoustic speed through the medium, e.g., an increasing or decreasing acoustic speed gradient. The coupling medium can have an acoustic speed including 900, 100, 1100, 1200, 1300, 1400, 1500, 1600, 1700, 1800, 1900, 2000, 2100, 5000, 10000, 15000, 20000 m/s or more, including all values and ranges there between and can include combinations and gradients of materials having variable acoustic speeds.

In certain imaging systems described herein multiple optical probes will be configured in various planes and directions with respect to each other to provide two dimensional and three dimensional images showing topographic shapes of the imaged objects or targets. Probe beams can be configured within various planes of the coupling medium and can be positioned at various distances from the probe/target interface.

Embodiments include an acoustic detector comprising: (a) a probe beam source that can generate an optical probe beam; (b) a coupling medium through which the optical probe beam travels and through which acoustic waves can propagate; and (c) a probe beam detector configured to detect deflection of the probe beam by an acoustic wave as the acoustic wave travels through the coupling medium. In certain aspects the optical probe beam has a diameter of 5 to 100 µm. In a further aspect, the probe beam with a diameter less than the characteristic ultrasound wavelength. The focus diameter of the optical probe beam is limited by the diffraction limit, but can be as small as possible given such a limit. Furthermore, a probe beam source can generate 1, 2, 3, 4, 5, 6, 7, or more optical probe beams. In a further aspect the detector can comprise 1, 2, 3, 4, 5, 6, 7, or more probe beam sources.

The acoustic detector can further comprise an array of micro-lenses positioned such that an optical probe beam is split into multiple columns. In certain aspects each probe beam is paired with a separate probe beam detector. In a further aspect the optical probe beam is laser. However, any apparatus for generating a structured light beam array such as using a prism assembly can be used as the source of the probe beams.

The probe beam detector is configured to detect probe beam deflection in two-dimensions. The detector can determine the pressure amplitude of an acoustic wave, the distance of the acoustic source, and direction of the acoustic wave. In certain aspects the detector is a photodiode. In further aspects the detector is a quadrant detector. In certain aspects the acoustic detector has a frequency response between 1, 10, 50, or 100 Hz to 1, 20, 60, 80, or 100 MHz, including all values and ranges there between. The acoustic detector can be at least, at most, or about 50, 100, 200, to 300, 400 or 500 µm, including all values and range there between, in diameter or larger.

The coupling medium is capable of transducing acoustic waves and will also allow traversal of probe beams. The coupling medium can be any material with an appropriate change of refractive index with change in pressure ($\Delta n/\Delta p$). In certain aspects, the coupling medium includes but is not limited to alcohol, glass, plastic, acoustic gel or any other acoustic transmitting medium that provides a transparent or semi-transparent medium so that a detectable amount of probe beam is transmitted to the detector. Coupling medium can include various liquids, gases, and solids. Examples of such coupling mediums includes, but is not limited to acetic acid, acetone, alcohols (e.g., butanol, ethanol, propyl alcohol, methanol and the like), benzene, carbon disulfide, carbon tetrachloride, castor oil, chloroform, ether, ethylene glycol, glycerol (glycerine), heptanes, hexane, kerosene, mercury, octane, phenol, toluene, turpentine, water (including various aqueous solutions such as salt solutions and the like), plastics, diamond, glass, pyrex, lucite, etc. In certain aspects characteristics of the coupling medium can be controlled or modulated by temperature, e.g. a coupling medium may have a different acoustic speed at 0° C. that at 37° C.

The acoustic detector can comprise one or more first probe beam sources and one or more second probe sources that can generate first and second probe beams that are non-parallel, parallel, planar, and/or non-planar. In certain aspect the probe beams can be perpendicular to each other. In certain aspects the second probe beam is orthogonal to the first probe beam.

Certain embodiments are directed to an acoustic detection system comprising: (a) an acoustic detector as described herein; (b) an excitation source configured to expose an imaging target to an excitation beam that interacts with the imaging target to generate acoustic signals from the imaging target. In certain aspects, the excitation source is pulsed laser source.

A method of imaging an object or subject comprising: (a) contacting a surface of the object or subject to be imaged with an acoustic detector of as described herein; (b) exposing a target area of the object or subject to be imaged to an excitation source so that the target area produces or reflects acoustic waves as a result of exposure to the excitation source; (c) detecting acoustic waves generated by a target area exposed to the excitation beam by probe beam deflection; and (d) constructing an image of the target area using the information provided by the detection of probe beam deflection. In certain aspects the subject is an animal, including a human. In a further aspect, a tissue is imaged, including but not limited to blood vessel, tumor, blood, gland, or a tissue comprising a foreign body. Essentially any object can be imaged that produces acoustic waves upon stimulation or exposure to a excitation beam. In certain aspects, the excitation source can be a light beam, acoustic waves, or any other energy source that is absorbed or reflected as acoustic waves.

In certain aspects the target is a biological target such as a tissue, organ, vessel, tumor, microbe, tissue section, biological fluid, or any other biologic material. In a further embodiment the target is a non-biological such as a non-biological liquid, gas, or solid. Non-biological targets include, but are not limited to industrial materials, various parts and components of machinery, automotive parts, engine parts, automotive frame, aircraft frames, spacecraft frames, propellers, reciprocating engines, gas turbine engines, construction materials, bridges, various machine parts, castings, forgings, pressure vessels, storage tanks, welds, boilers, heat exchangers, turbines, pipes, piping, railways, rail inspection, wheel inspection, amusement park rides, water craft, submarines, warships, and the like. The excitation beam will be selected based on the properties of the target and the purpose of the test being performed.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 4A) exposing a tissue block containing an absorbing object to a laser pulse. (FIG. 4B) Generation and propagation of pressure waves after excitation in spherical coordinates. The pressure waves are detected by deflection measurements of three position sensors (FIG. 4C), from which the optoacoustic image can be reconstructed. Quadrant position detector 401, Probe beam(s) 406, excitation beam 408, Coupling medium 409, Tissue phantom 404, Acoustic wave 407.

(FIG. 5B) Deflection events occurring at probe beam 2, as an example showing the reconstruction of the relative location of the source objects, based on the time delay between the arrivals of the pressure waves from each source object, which produce deflection of the probe beam.

DETAILED DESCRIPTION OF THE INVENTION

Figure 1:
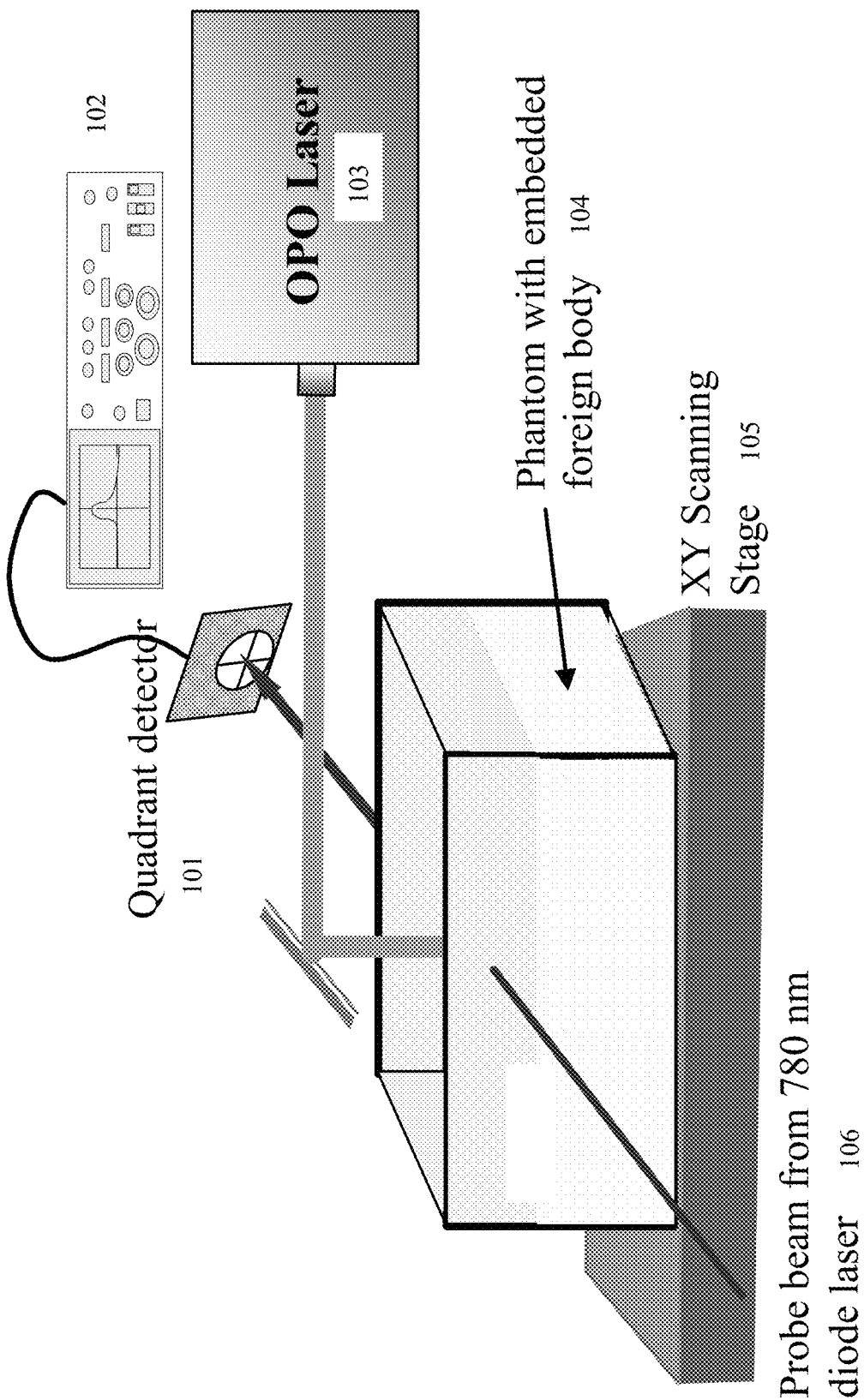
FIG. 1. Illustrates a general configuration for monitoring the deflection of an optical probe beam. Quadrant detector 101, controller 102, OPO laser 103. Phantom with embedded foreign body 104, XY Scanning stage 105, prode beam 106.

Optical sensors based on probe beam deflection technique (PBDT) are an accurate non-contact and non-destructive method, permitting measurements in hostile environments and allowing remote sensing. Usually most of the piezoelectric transducer used for imaging suffers from a ringing effect which follows the actual signal, which limits their time resolution and sensitivity, it is often a complicated analysis and algorithm is needed to construct an image. Further, optical sensors are insensitive to background noise, minimizing the need for acoustic isolation or shielding.

Optical probes have high axial resolution comparing to piezoelectric transducers, which allows the use multi of optic probes next to each other to provide high resolution and much faster image recording—resulting in a reduced need for scanning the target. Optical probes can be configured to surround a target resulting is no need to rotate the target to image in three dimensions. Utilizing multiple sensors as described herein 3-D optoacoustic image can be constructed.

The optical sensors have the ability to measure three parameters at the same time: pressure amplitude, the distance of optoacoustic source by measuring the time delay after excitation, and location or direction from the source of the optoacoustic wave. The ability to measure the direction angle where the acoustic signal is traveling from is unique and can be employed to provide a higher resolution system. In addition using an optical system does not limit or block the access of an excitation source (e.g., excitation beam) because the sensors are outside the target area.

In certain applications a target is illuminated with short laser pulses. The light is scattered inside the target and heats absorbing structures. Because of the thermoelastic effect, the heating generates pressure transients representing the absorbing structures. These ultrasound transients propagate to the surface and can be measured with an acoustic transducer.

A key element of every acoustic system is the ultrasound transducer. Classically ultrasound transducers are made from piezoelectric materials, which allow a direct conversion of pressure into voltage. Piezoelectric materials, such as Lead Zirconate Titanate (PZT), and Polyvinylidene Fluoride (PVDF) have high conversion efficiency. Medical ultrasound applications have motivated development of linear and even two-dimensional arrays piezoelectric transducers. Manufacturing difficulties, however, limit the minimum element size and element number of such probes.

These limitations have encouraged the development an optical methods for imaging with high sensitivity and resolution—the probe beam deflection technique (PBDT). The principle of this technique is the detection of a refractive index gradient produced by the heating and expansion of a sample as a result of absorbed laser radiation by detecting a static thermal lens produced by heating of a material through which probe beams travel. See U.S. Pat. No. 4,468,136, which is incorporated herein by reference in its entirety.

The basic theory of the PBDT states that when there is a pressure gradient passing through a focused probe beam, the change of the optical refractive index of the coupling media n can be approximated by:

$$n(p) = n_0 + \frac{\partial n}{\partial p} p$$

where $n_0$ represents the normal refractive index of undistributed media. The deviation angle $\varphi$ of the probe beam crossing a region with refraction index gradient $\nabla n$ (considered spatially constant over the beam cross-section) is given by:

$$\phi = \frac{1}{n_0} \int \nabla_\perp n \, ds$$

where the integral is calculated on the ray path through the interaction region, the symbol $\perp$ denotes the projection of the gradient on the direction perpendicular to the ray. Assuming a Gaussian $TEM_{00}$ probe beam, the deflection signal $\Delta V$ sensed by the photodiode depends on the deflection angle $\varphi$ according to the following expression:

$$\Delta V(t) = V_0 \text{erf}(\sqrt{2}\varphi(t)\pi w/\lambda)$$

where erf denotes the error function, $V_0$ is photodiode voltage, w is the focal spot size, and $\lambda$ the wavelength of the probe beam.

As described herein, the inventor has developed a non-invasive, contact transducer developed to couple to objects or biological tissues or samples both optically and acoustically. PBDT is used to record the acoustic signals. The principle of this technique is the detection of a refractive index gradient produced by an acoustic wave. PBDT is an accurate non-contact and non-destructive method that permits measurements in hostile environments and allows remote sensing. It is simple to align and it is insensitive to background noise, minimizing the need for acoustic isolation or shielding. An illustration of such by monitoring the deflection of an optical probe beam is shown in FIG. 1.

Figure 2:
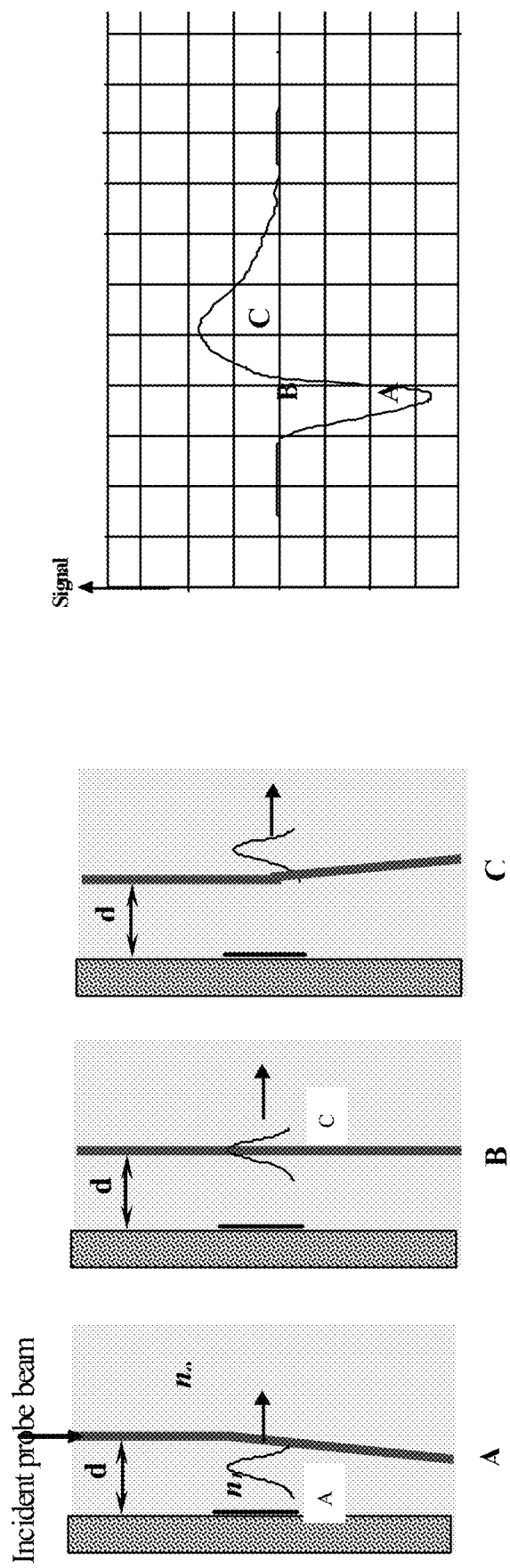
FIG. 2. Illustrates detection of a pressure wave by probe beam deflection as it propagates through the detection chamber and interacts with the probe beam. The propagation of this pressure wave produces a local density gradient, which alters the refractive index of the medium, leading to beam deflection. When the front of the acoustic wave passes through the probe beam it causes an increase in the media refractive index $n_0$ to $n_1$, which consequently deflects the probe beam towards the higher density region, forming the "negative lobe" of the signal (FIG. 2A). During the trailing edge of the wave the probe beam bends in the opposite direction producing the "positive lobe" due to the decreasing density gradient. Subsequently the beam returns to its initial position as the wave propagates beyond the interaction region (FIG. 2C).

In the case of the PBDT method, a pressure wave is detected indirectly, as it propagates through the detection chamber or medium and interacts with the probe beam. The propagation of this pressure wave produces a local density gradient, which alters the refractive index of the medium, leading to beam deflection. When the front of the acoustic wave passes through the probe beam it causes an increase in the media refractive index $n_0$ to $n_1$, which consequently deflects the probe beam towards the higher density region, forming the "negative lobe" of the signal (FIG. 2A). During the trailing edge of the wave the probe beam bends in the opposite direction producing the "positive lobe" due to the decreasing density gradient. Subsequently the beam returns to its initial position as the wave propagates beyond the interaction region (FIG. 2).

The technique can be demonstrated by using a simple, laboratory-built position sensors. In determining the vector direction of a pressure wave source, a 2-D quadrant detector with fast electronics and low noise for multiple probes can be used. Wide bandwidth position sensors, with a frequency response 1-100 MHz can be custom fabricated for this purpose. Quadrant detector photodiodes are inexpensively available from several sources.

Figure 3:
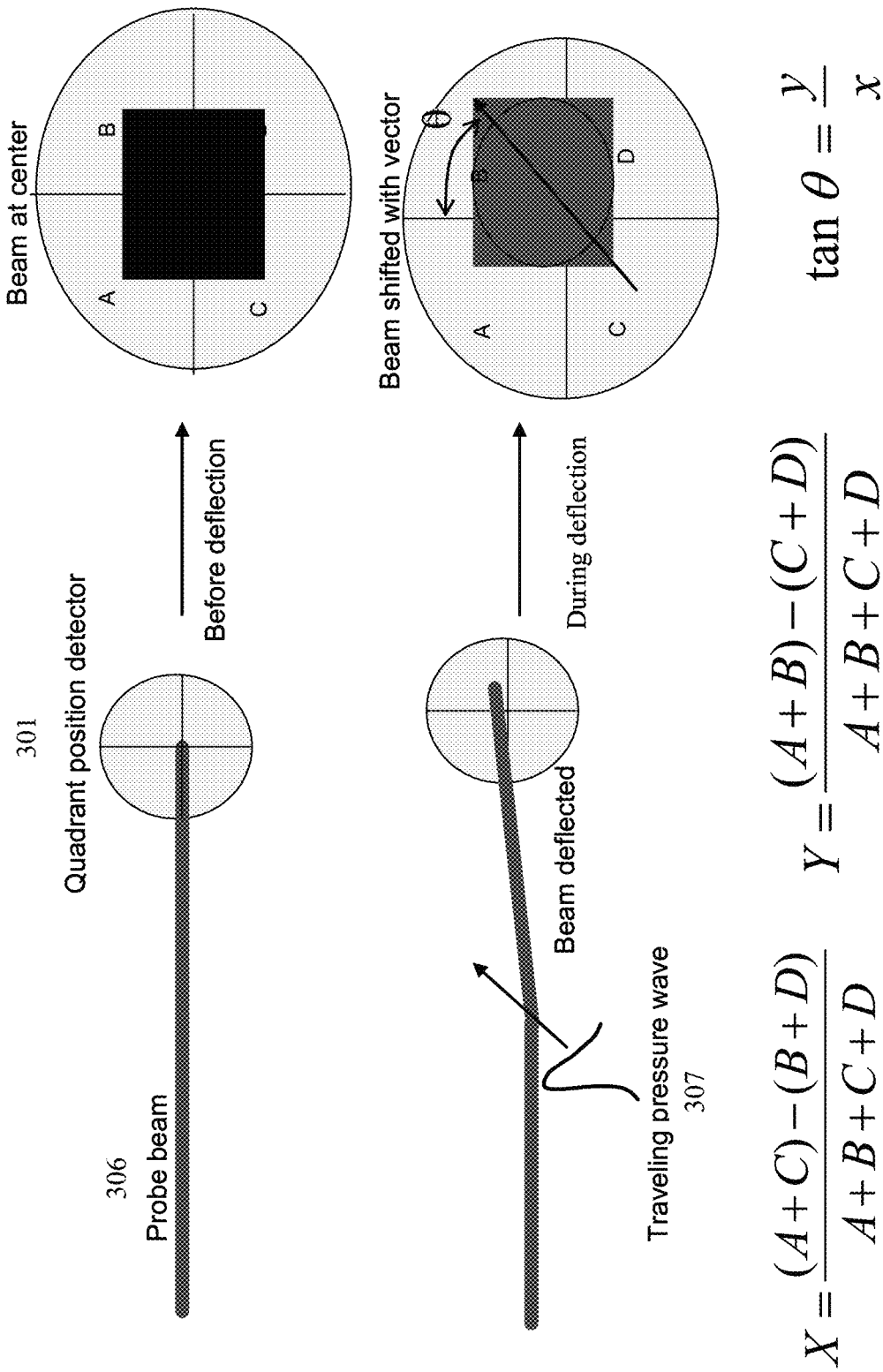
FIG. 3. Schematic example of the ability of the probe beam deflection technique (PBDT) to measure pressure wave direction using a quadrant position detector. Quadrant position detector 301, Probe beam 306, traversing pressure wave 307.

The following discussion describes how vector information can be obtained using position detectors. FIG. 3 shows an example of a case in which a pressure wave is traveling at an angle with respect to the position of the probe beam, causing the beam to be tilted from the center of the quadrant detector to position B on the detector (2 o'clock position). The vector angle of the probe beam deflection may be determined by calculating the X and Y position of the light with respect to the center as follows:

$$X = \frac{(A+C)-(B+D)}{A+B+C+D}, \quad (1)$$
$$Y = \frac{(A+B)-(C+D)}{A+B+C+D}$$

Thus three parameters can be measured using a single probe beam: pressure amplitude, the distance of optoacoustic source by measuring the time delay after excitation, and location or direction from the source of the optoacoustic wave. In addition, by utilizing scanning or multiple sensors, it is possible to construct 3-D optoacoustic images.

The ability to measure the angular direction of the acoustic wave is unique to the PBDT, compared to other conventional method of acoustic imaging. The small spot size of the probe beam (5-100 μm diameter) can provide high axial resolution, compared to ultrasonic transducers of circular shape, without sacrificing sensitivity for the small size.

Figure 4:
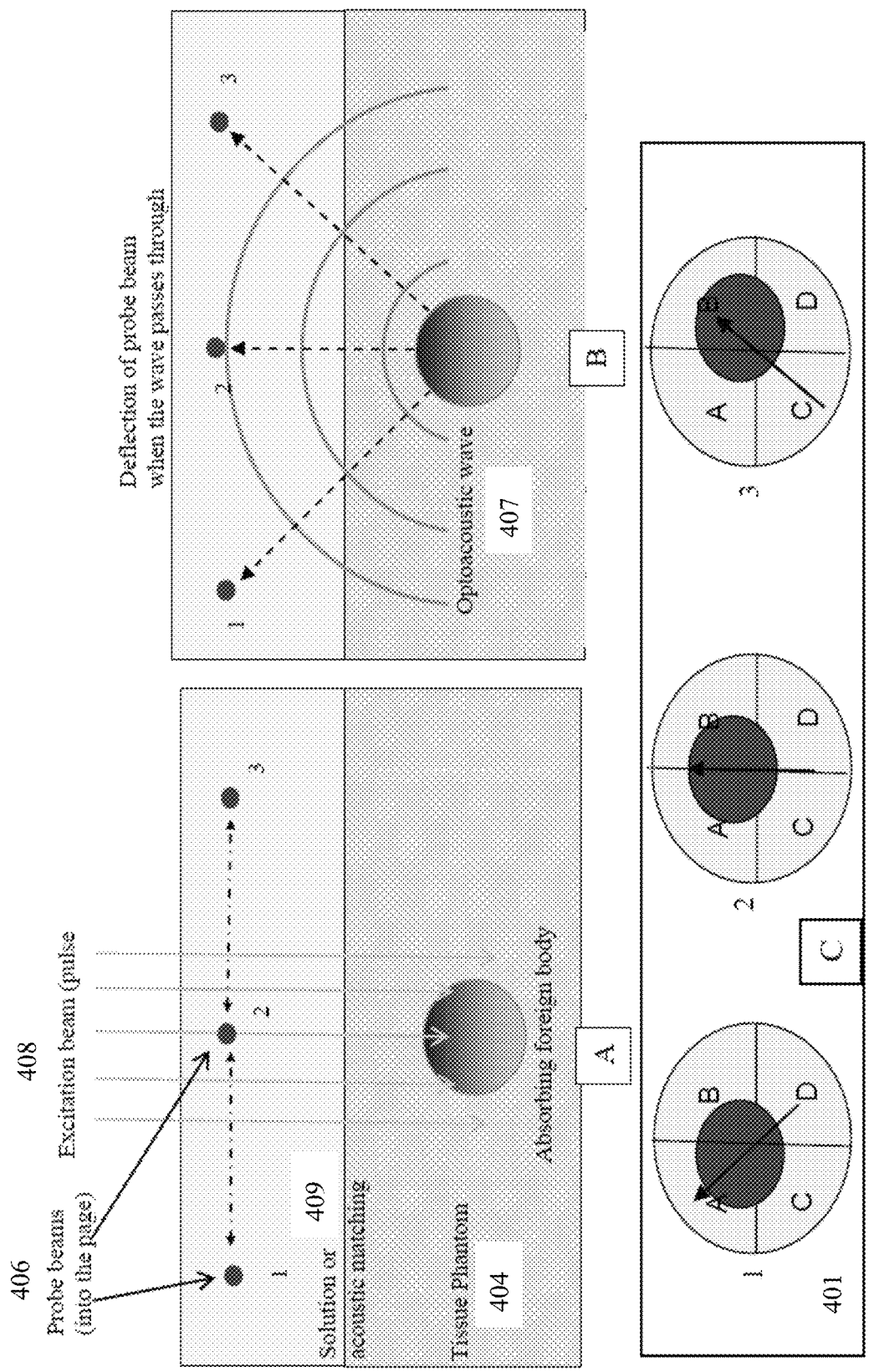
FIG. 4. Schematic diagram of an example of using three probe beams for optoacoustic imaging.

In addition, fast or real-time images can be constructed by using multiple optical probe beams, with less required scanning time. FIG. 4 shows an example of using three probe beams to trace and construct an acoustic image, induced optoacoustically in a biological tissue containing a spherical or cylindrical shaped absorber. FIG. 4A shows the pulsed excitation laser beam entering the tissue with the embedded absorber, and three probe beams pass through a solution of acoustic medium above the tissue in the horizontal direction (i.e., into the page). Three position sensors are used in this example—one for each probe beam.

After exposure to the laser the upper side of the object is heated and the resulting thermoelastic expansion produces an acoustic pressure wave taking the shape of the source (FIG. 4B). The acoustic wave will propagate through the surrounding medium with minimum acoustic loss. The pressure wave will arrive first at probe beam #2, causing a beam deflection along the vertical axis. At a later time, depending, on the propagation delay through the tissue, the deflection of probe beams #1 and #3 will occur simultaneously or with a time difference, depending on the location of the source relative to these two probe beams. By analyzing the delay time, deflection amplitude, and the source angle a 3-D image of the shape of the source can be reconstructed. To reconstruct a higher resolution image scanning the distance between the probe beam to cover the whole space area can be implemented. Using multiple probe beams will reduce the time to construct imaging using the PBDT.

Figure 5:
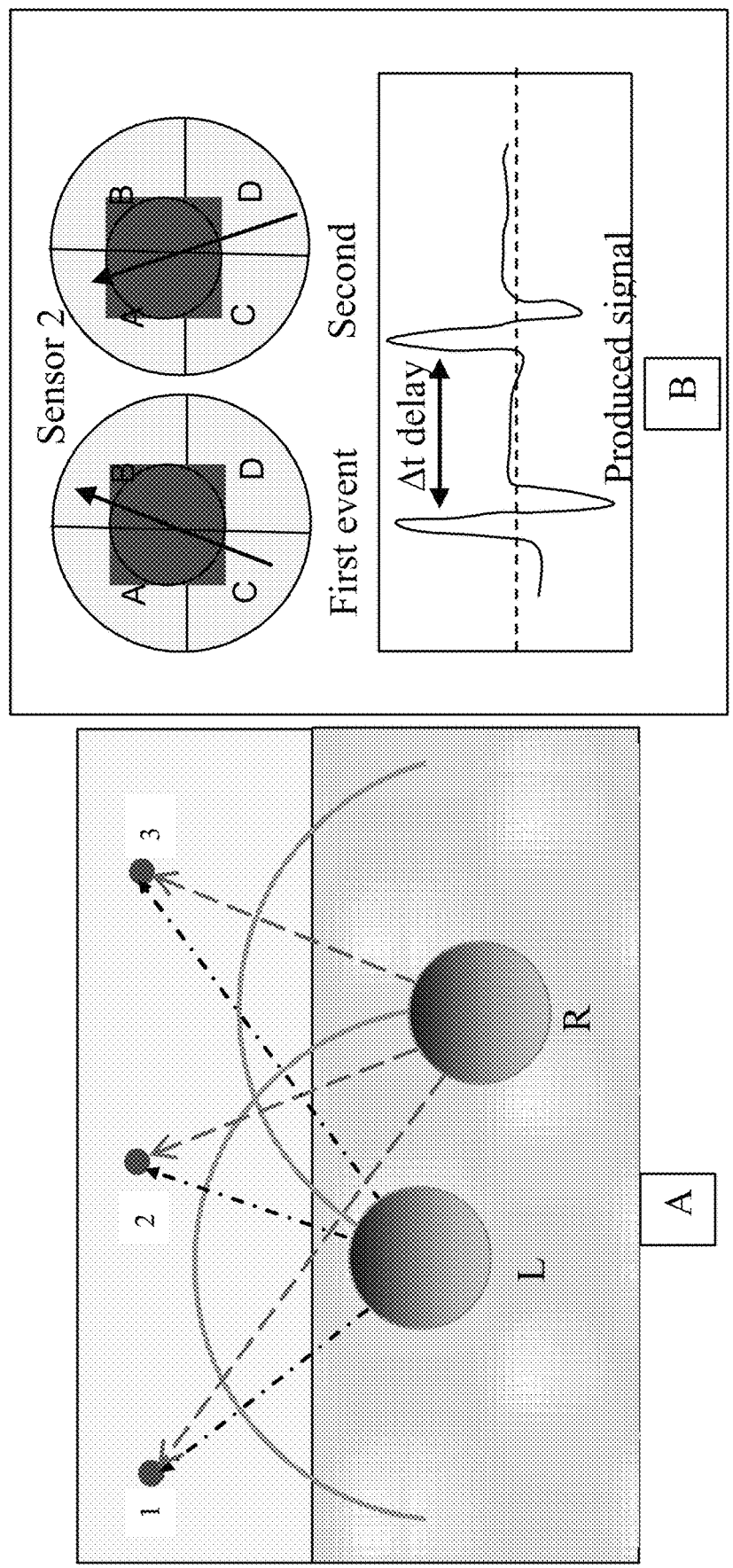
FIG. 5. Schematic diagram of an example of using three probe beams for optoacoustic imaging (FIG. 5A) Generation and propagation of pressure waves after excitation of two absorbing spherical objects.

FIG. 5 illustrates another example of using the three probe beams when two absorbing objects are excited by light with the same setup as in FIG. 4. Every probe beam will sense two deflections, because two waves are generated at the same time. The sensor differentiates the signals from the two sources by determining the direction of propagation of the wave and the time delay, Δt, between the signals. The analysis of the events occurring at probe 2 as the first wave is generated from the sphere L is illustrated—sensor 2 is closer to object L. The pressure wave traveling from object L deflects probe beam #2 toward photodiode B, where the exact angle can be calculated. After a time delay a second deflection occurs as a result of the acoustic wave from the source R, where the probe beam is deflected toward photodiode A. Following the arrows in FIG. 5A from both sources, the events occurring at each probe will provide enough information to project the optoacoustic image.

Figure 6:
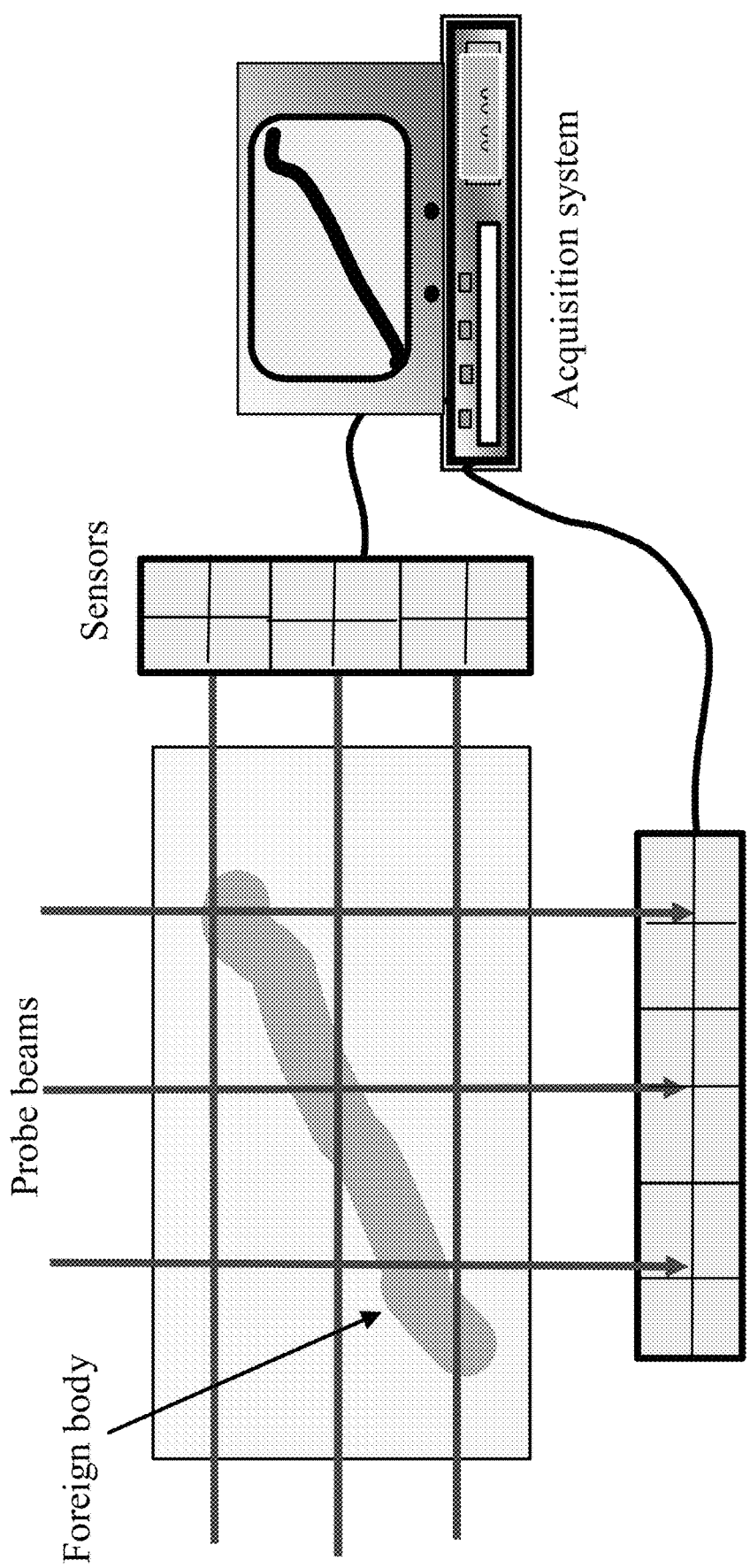
FIG. 6. Schematic setup using the PBDT in both X and Y axes (beams and sensors on opposite sides).
Figure 7:
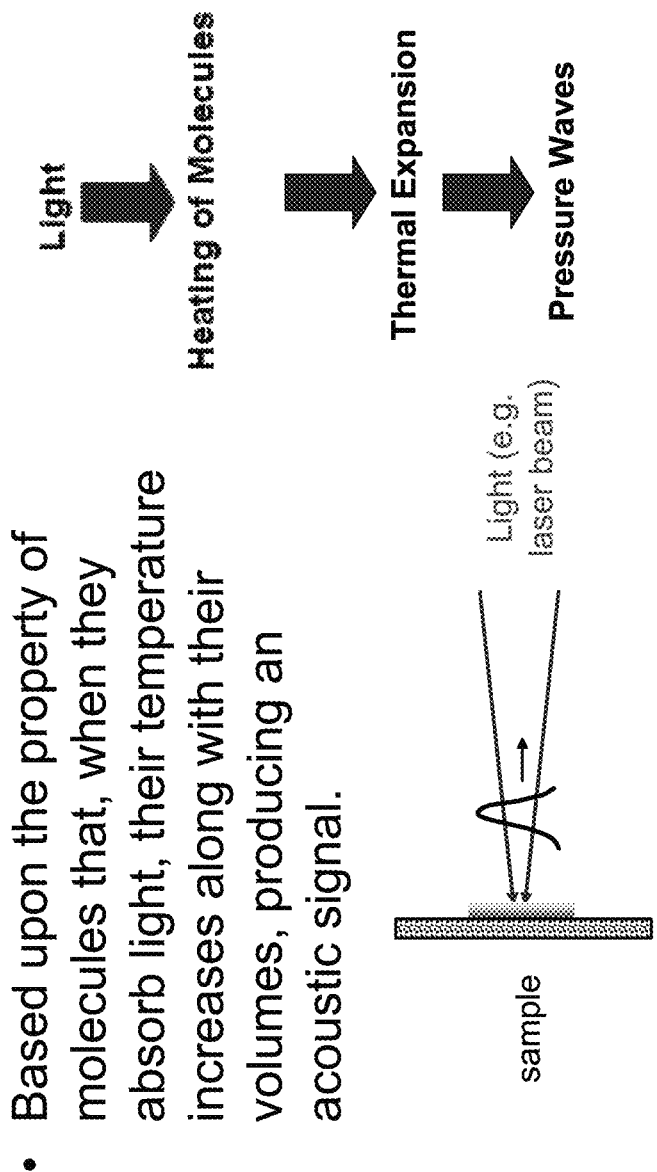
FIG. 7. Schematic of the general principle of optoacoustics.
Figure 8:
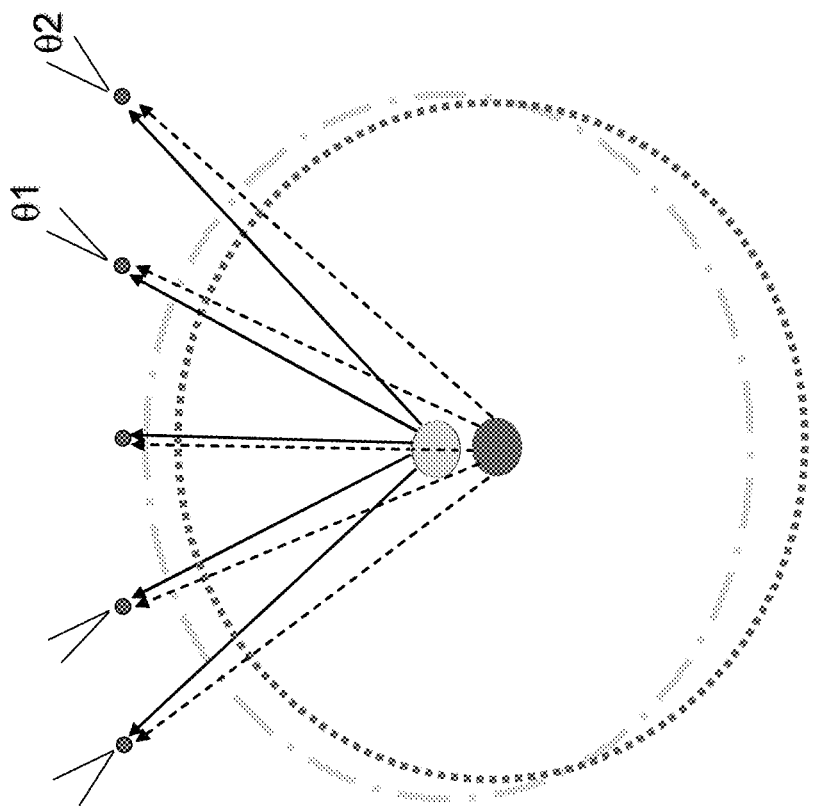
FIG. 8. Schematic diagram of an example of using multi probe beams for optoacoustic imaging to enhance the axial resolution when angular information is used depending in the location of the probe beam from the target.
Figure 9:
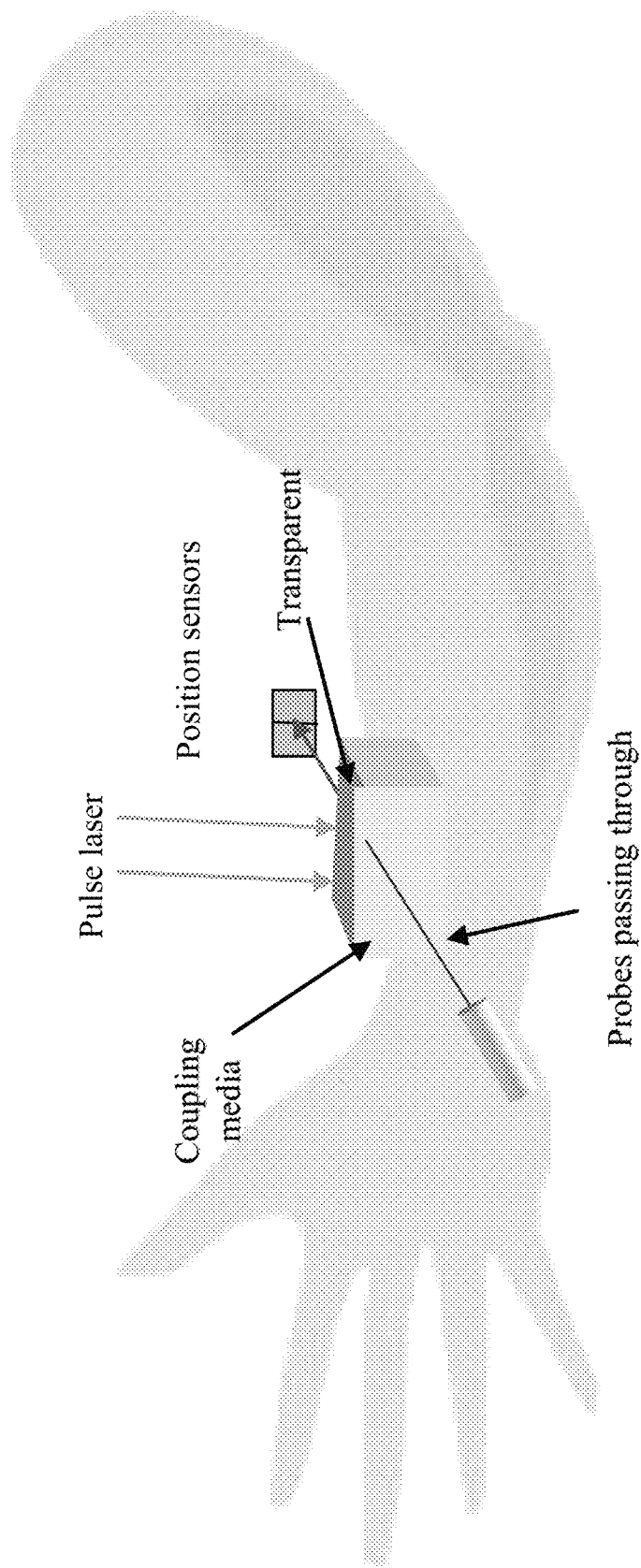
FIG. 9. Schematic of a handheld acoustic detector.

A more sophisticated system of optical sensors can be designed using multiple probe beams in the X and Y axes or the X, Y, and Z, rather than in only one axis. The beams may pass through an acoustic coupling medium in contact with the target. In certain aspect the transducer can be coupled to the target with an acoustic gel. FIG. 6 shows an example setup using three probe beams in the X and Y axes. This setup provides more information regarding acoustic propagation generated using the techniques described herein.

The systems described can include, but is not limited to, at least one energy emitter component or excitation source, including one or more thermal energy emitters, electromagnetic energy emitters (e.g., laser), electrical energy emitters that can be used to stimulate or result in acoustic waves being emitted or reflected from an imaging target.

Figure 10:
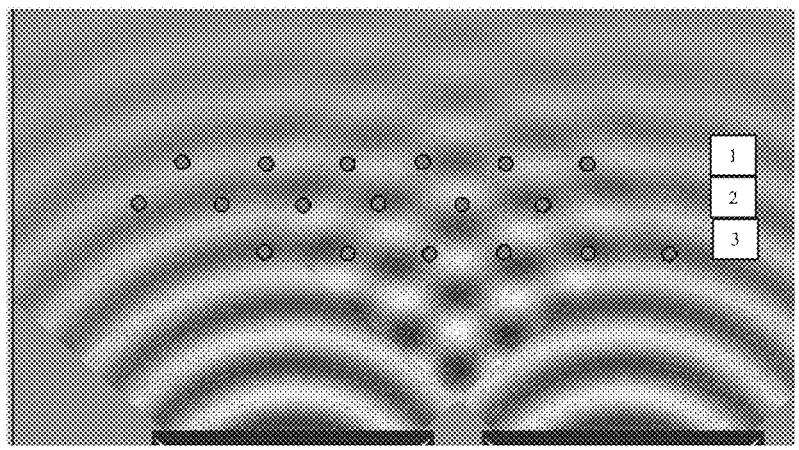
FIG. 10. Acoustic wave interference can be resolved and monitored by optical sensors (dots going into the page) passing through the interaction region of coupling medium.

Certain embodiments are directed to three dimensional arrays (probe beams in the X, Y, and Z axis, see FIG. 11) of optical sensors to monitor and record acoustic/pressure/ultrasound waves: They are many advantages to non-contact ultrasound sensors. One such advantage is the ability to configure sensors in a variety of arrays. The sensor can be configured in such a way to improve resolution of interference and diffraction patterns see FIG. 10. The probe beams in FIG. 10 are passing through the medium at locations of constructive interference and others in locations of destructive interference. The ability to monitor the pressure wave without mechanically changing its amplitude or other properties allows the layering of sensors (i.e., arrangement of sensors at various distances from the probe target interface) to monitor the changes of the pressure wave in different locations at different times. Such a configuration provides more information about the propagation of pressure wave and allows back reconstruction of the source of pressure wave. This layering of sensors can also provide faster time to image. In certain aspects at least 2, 3, 4, 5, 6, 7, 8, 9, 10 or more layers of at least 1, 2, 3, 4, 5, 6, 7, 8, 9, 10 or more sensors can be used in a probe as described herein.

Other advantages of these layered configurations include the enhancement of sensitivity. The signal from the first, second, and third or more layers at known locations in the probes can be used to increase the signal to noise ratio when pressure amplitude value added and averaged when taking into account different locations and distances of sensors. For example, two sensors layered above each other with a 3 mm distance between them, when monitoring a single pressure wave, will detect and record a pressure wave at the proximal layer of sensors first. An attenuated signal with a time delay of (3 mm/(speed of sound in medium)) will be detected and recorded at the second layer of sensors. The signal from both sensor layers can processed with a mathematical algorithm to improve the signal to noise ratio.

Figure 11:
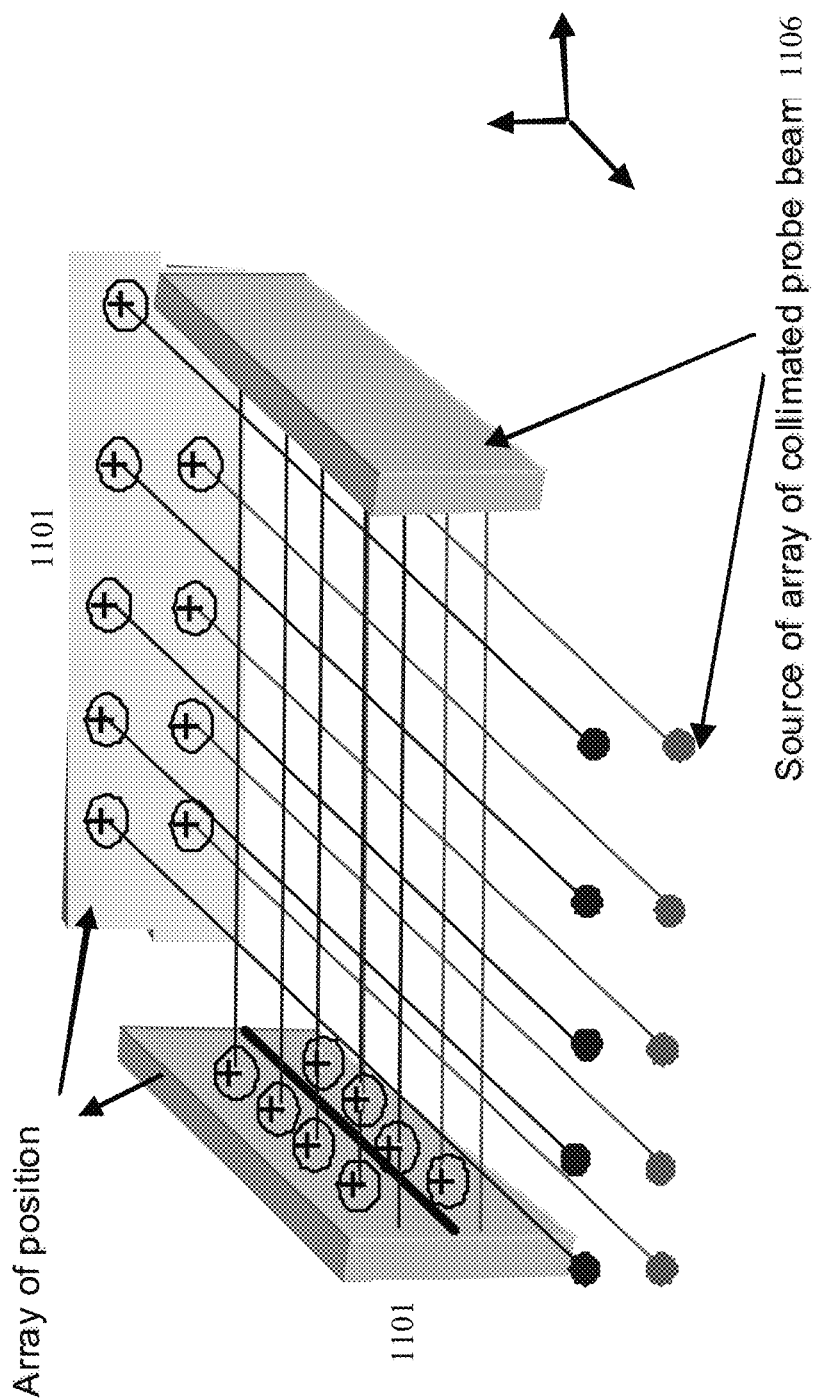
FIG. 11. 3-D powerful ultrasound head sensor based on optical probes. Quadrant position detector(s) 1101, Probe beam(s) 1106.

FIG. 11 illustrates an example of an ultrasound probe containing a three dimensional configuration of sensors using an X, Y, and Z plane. Each plane is associated with their own probe beam which is collimated to each other. Also illustrated in FIG. 11 are multilayer sensors positioned in the Z axis respective to the probe interface. Each probe beam is centered with respect to its sensor, thus when interacting with a pressure wave each sensor can detect and record the probe beam defection(s) associated with its particular position. This three dimensional array of probe beams will pass through a transparent coupling medium, such as water. Such a method can be compared to a holographic imaging of acoustic propagation through the ultrasound head sensor.

Figure 12:
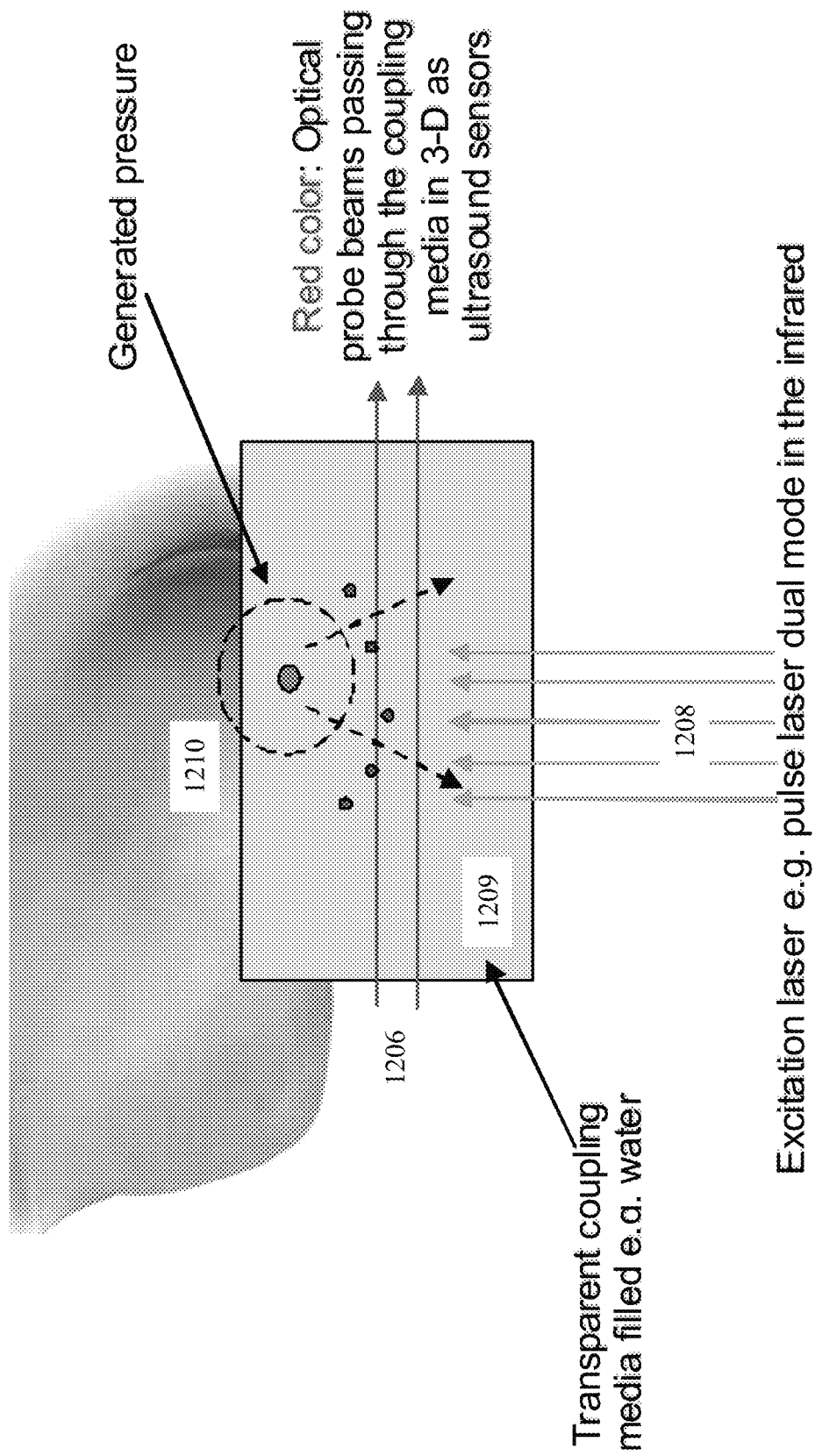
FIG. 12. Example of possible arrangement of optoacoustic imaging system based on optical probes for breast imaging. Probe beam(s) 1206, Excitation beam(s) 1208, Coupling medium 1209, Tissue 1210.
Figure 13:
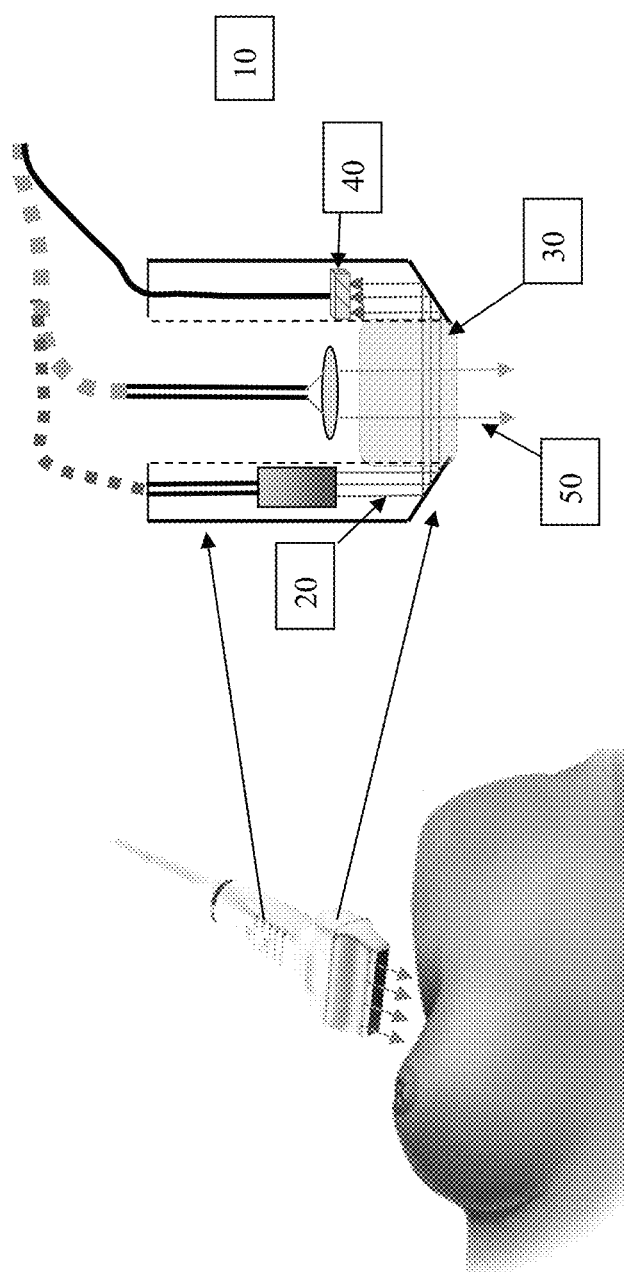
FIG. 13. Handheld optoacoustic imaging sensor based on the probe beam deflection technique.

A three dimensional probe, such as that described above, can be coupled in a variety of different arrangements depending on the application. FIGS. 12 and 13 show an example of such a probe for photoacoustic/optoacoustic breast imaging. The breast can be free or compressed and contacted with probe that is operatively coupled to an excitation laser. The probe beams can be configured to surround the breast. The advantage of using remote acoustic pressure sensors can be appreciated where space is available in front of the imaging object to be utilized by the excitation laser and other tools such as camera.

FIG. 13 illustrates a modified handheld ultrasound sensor 10 that can be used in conjunction with the methods and apparatus described herein. The optical sensor arrangement can be built in a compact and rigid handheld device that is useful for applications such as breast or skin imaging. FIG. 13 illustrates an array of probe beam 20 passing through a coupling medium 30 after reflection and then reflect again to the position sensor 40. Prisms with total internal reflection or mirrors can be used to reflect the probe beams as illustrated. The coupling medium can be made from material with good ultrasound transmission and optical transparency for the desired optical wavelengths of the excitation beam 50 and probe beam wavelengths.

Certain embodiments of the invention can be used in photoacoustic imaging and microscopy. Photoacoustic imaging, as a hybrid biomedical imaging modality, is developed based on the photoacoustic effect. In photoacoustic imaging, non-ionizing laser pulses are delivered into biological tissues (when radio frequency pulses are used, the technology is referred to as thermoacoustic imaging). Some of the delivered energy will be absorbed and converted into heat, leading to transient thermoelastic expansion and thus wideband (e.g. MHz) ultrasonic emission. The generated ultrasonic waves are then detected by the apparatus described herein to form images.

The optical absorption in biological tissues can be due to endogenous molecules such as hemoglobin or melanin, or exogenously delivered contrast agents such as gold nanoparticles. Since blood usually has orders of magnitude larger absorption than surrounding tissues, there is sufficient endogenous contrast for photoacoustic imaging to visualize blood vessels. Recent studies have shown that photoacoustic imaging can be used in vivo for tumor angiogenesis monitoring, blood oxygenation mapping, functional brain imaging, and skin melanoma detection etc.

A representative photoacoustic microscopy (PAM) set-up can include a tunable dye laser. A short laser pulse at a certain wavelength between 532-770 nm is generated to irradiate the target tissue to induce acoustic pressure waves. Laser pulses of ~6 mJ/cm$^2$ at the focus can be delivered at 10 Hz repetition rate. An optical fiber can be coaxially positioned on a three-dimensional mechanical stage with a detection apparatus as described herein. The imaging depth of PAM is mainly limited by the ultrasonic attenuation. The spatial and lateral resolutions depend on the detectors used.

PAM has multiple important applications in functional imaging. Two examples are the detection in changes in oxygenated/deoxygenated hemoglobin in small vessels and the imaging of skin melanoma to obtain the morphological relationship between the melanoma and its surrounding blood vessels structures in vivo.

Aspects of the invention can be used in nondestructive testing (NDT). NDT is a wide group of analysis techniques used in science and industry to evaluate the properties of materials, components, or systems without causing damage. Because NDT does not permanently alter the article being inspected, it is a highly-valuable technique that can save both money and time in product evaluation, troubleshooting, and research. Common NDT methods include ultrasonic, magnetic-particle, liquid penetrant, radiographic, remote visual inspection (RVI) and eddy-current testing. NDT is a commonly-used tool in forensic engineering, mechanical engineering, electrical engineering, civil engineering, systems engineering, aeronautical engineering, medicine, and art.

The apparatus and methods described herein can be used for NDT of various non-biological targets. For instance, modern engineering, particularly in the transport industry, is requiring materials to be lighter while withstanding greater stress and strain due to increased load, faster operating speeds and more intense working timetables. The desire to reduce vehicle weight has led to greater use of composite materials and in particular laminated materials and many of the non-destructive testing techniques that have previously been developed for metal parts are rather inadequate for detecting defects in composite parts and the test may take significant periods to set up because of complex testing techniques. Developments in creating composite materials have expanded the use of composite materials into a wide variety of applications. Because of its high strength and durability combined with its low weight, composites are replacing metals and metal alloys as the base material for certain load bearing components. For example, composites are now commonly used as a material for body parts and structure in vehicles such as automobiles, watercraft, and aircraft. However, to ensure composite mechanical integrity, strict inspections are required. The inspections are typically required upon fabrication of a component made from a composite and periodically during the life of the component. Composite or metal materials, components, or parts, including, but not limited to materials such as pipes, bars, sheets, and other fabrications.

In manufacturing, it is common to join two or more materials. For instance, welds are used to join two or more metal surfaces. Because these connections may encounter loads and fatigue during product lifetime, there is a chance that they may fail if not created to proper specification. For example, the base metal must reach a certain temperature during the welding process, must cool at a specific rate, and must be welded with compatible materials or the joint may not be strong enough to hold the surfaces together, or cracks may form in the weld causing it to fail. The typical welding defects, lack of fusion of the weld to the base metal, cracks or porosity inside the weld, and variations in weld density, could cause a structure to break or a pipeline to rupture. Welds may be tested using NDT techniques based on the apparatus described herein.

The invention claimed is:

1. A handheld ultrasound probe comprising:
   a probe body having:
   (a) a coupling medium configured to form an interface between the probe and an imaging target during use, the coupling medium having a refractive index that changes when there is a change in pressure in the coupling medium due to an acoustic wave, transmitted from the target, passing through the coupling medium when the the handheld ultrasound probe is in use;
   (b) a quadrant light sensor and a probe beam source, wherein the probe beam source is configured to generate a probe beam that travels through the coupling medium to the quadrant light sensor, the probe beam being deflected by the change of refractive index in the coupling medium when the handheld ultrasound probe is in use; and
   (c) an excitation beam source configured to produce an excitation beam during used, wherein the excitation beam interacts with a target to generate acoustic waves in the target.

2. The handheld ultrasound probe of claim 1, wherein the probe beam source generates a probe beam having a diameter of 1 to 100 μm.

3. The handheld ultrasound probe of claim 1, wherein the probe beam source generates two or more probe beams.

4. The handheld ultrasound probe of claim 3, wherein the probe beams are configured to traverse the coupling medium in different planes with respect to a coupling medium/target interface.

5. The handheld ultrasound probe of claim 1, further comprising two or more probe beam sources.

6. The handheld ultrasound probe of claim 1, further comprising an array of micro-lenses positioned such that an optical probe beam is split into multiple columns.

7. The handheld ultrasound probe of claim 1, wherein the probe beam source is a laser.

8. The handheld ultrasound probe of claim 7, wherein the laser has a wavelength of 200 nm to 1000 nm.

9. The handheld ultrasound probe of claim 1, wherein the quadrant light sensor has a frequency response between 1 Hz to 100 MHz.

10. The handheld ultrasound probe of claim 1, wherein the quadrant light sensor is 50 to 500 μm in diameter.

11. The handheld ultrasound probe of claim 1, wherein the coupling medium is alcohol, glass, plastic, or an acoustic gel.

12. The handheld ultrasound probe of claim 1, wherein the acoustic detector further comprises a second probe beam source that can generate a second probe beam that is non-parallel to the first probe beam.

13. The handheld ultrasound probe of claim 12, wherein the second probe beam is orthogonal to the first probe beam.

14. An imaging system comprising the handheld ultrasound probe of claim 1, operatively coupled to an image processing module.

15. A method of imaging an object or subject comprising:
   (a) contacting a surface of the object or subject to be imaged with the handheld ultrasound probe of claim 1;

(b) exposing a target area of the object or subject to be imaged to an excitation source so that the target area produces or reflects acoustic waves as a result of exposure to the excitation source;
(c) detecting acoustic waves generated or reflected by the target area exposed to the excitation source by probe beam deflection using the acoustic detector handheld ultrasound probe of claim 1; and
(d) constructing an image of the target area using information provided by the handheld ultrasound probe of claim 1.

16. The method of claim 15, wherein the target is a blood vessel, a tumor, blood, a gland, an organ, or a tissue comprising a foreign body.

17. The method of claim 15, wherein the object is a non-biological material.

\* \* \* \* \*